United States Patent
Safonov

(10) Patent No.: US 11,904,124 B2
(45) Date of Patent: Feb. 20, 2024

(54) SYSTEMS AND METHODS FOR TOPICAL APPLICATION OF MOLECULAR HYDROGEN

(71) Applicant: Vladimir L. Safonov, Grandbury, TX (US)

(72) Inventor: Vladimir L. Safonov, Grandbury, TX (US)

(73) Assignee: H2 Universe, LLC., Granbury, TX (US)

( * ) Notice: Subject to any disclaimer, the term of this patent is extended or adjusted under 35 U.S.C. 154(b) by 984 days.

(21) Appl. No.: 16/376,894

(22) Filed: Apr. 5, 2019

(65) Prior Publication Data

US 2019/0308001 A1    Oct. 10, 2019

Related U.S. Application Data

(60) Provisional application No. 62/819,943, filed on Mar. 18, 2019, provisional application No. 62/761,752, filed on Apr. 6, 2018.

(51) Int. Cl.
*A61M 35/00* (2006.01)

(52) U.S. Cl.
CPC .......... *A61M 35/30* (2019.05); *A61M 2202/02* (2013.01)

(58) Field of Classification Search
CPC .......... A61M 35/30; A61M 2039/0027; A61M 2210/04; A61M 5/1409; A61M 35/00; A61M 35/10; A61M 2202/02; A61H 2033/148
See application file for complete search history.

(56) References Cited

U.S. PATENT DOCUMENTS

| 8,852,660 B2 | 10/2014 | Miljkovic |
| 10,076,540 B1 | 9/2018 | Perricone |
| 2009/0326447 A1* | 12/2009 | Joshi ...................... A61K 31/00 604/82 |

(Continued)

OTHER PUBLICATIONS

Shingo Kanehira,*, Susumu Kanamori, Kohji Nagashima, Takashi Saeki, Heidy Visbal,Toshimi Fukui, Kazuyuki Hirao, "Controllable hydrogen release via aluminum powder corrosion in calcium hydroxide solutions", Aug. 27, 2013, Journal of Asian Ceramic Societies, pp. 296-303. (Year: 2013).*

(Continued)

*Primary Examiner* — Kami A Bosworth
*Assistant Examiner* — Antarius S Daniel
(74) *Attorney, Agent, or Firm* — Morgan, Lewis & Bockius LLP

(57) ABSTRACT

A hydrogen-delivering system for topical application of molecular hydrogen is provided. The system includes a housing that comprises at least one dry chemical and a liquid composition sealed therein, and that is configured to be attached to a target area of a subject's skin. The dry chemical and the aqueous composition are separated within the housing until the system is activated and the dry chemical and the aqueous composition are mixed to generate molecular hydrogen. The molecular hydrogen passes through a skin-facing surface of the housing, which is permeable to hydrogen and not permeable to the dry chemical and the aqueous composition, and is delivered to the subject's body.

10 Claims, 6 Drawing Sheets

(56) References Cited

U.S. PATENT DOCUMENTS

| | | | |
|---|---|---|---|
| 2010/0152683 A1* | 6/2010 | Lindgren | A61P 31/10 141/2 |
| 2010/0272789 A1* | 10/2010 | Satoh | A61P 17/18 424/618 |
| 2013/0323190 A1 | 12/2013 | Ohta et al. | |
| 2018/0092816 A1 | 4/2018 | Perricone et al. | |

OTHER PUBLICATIONS

B. C. Yang, Y. J. Chai, F. L. Yang, Q. Zhang, H. Liu, N. Wang, "Hydrogen generation by aluminum-water reaction in acidic and alkaline media and its reaction dynamics" Jan. 18, 2018, International Journal of Energy Research, pp. 1594-1602. (Year: 2018).*

Huang, et al., "Recent advances in hydrogen research as a therapeutic medical gas," Free Radical Research, 44(9): Sep. 2010, pp. 971-982.

Ohta, "Recent Progress Toward Hydrogen Medicine: Potential of Molecular Hydrogen for Preventive and Therapeutic Applications," Current Pharmaceutical Design, 17, 2011, pp. 2241-2252.

Safonov, et al., "Hydrogen nanobubbles in a water solution of dietary supplement," Colloids and Surfaces A: Physicochemistry Engineering Aspects, vol. 436 (2013), pp. 333-336.

Dixon, et al., "The evolution of molecular hydrogen: a noteworthy potential therapy with clinical significance," Medical Gas Research, vol. 3, No. 10, 12 pages, 2013.

Kanehira, et al., "Controllable hydrogen release via aluminum powder corrosion in calcium hydroxide solutions," Journal of Asian Ceramic Societies 1 (2013) 296-303.

Kobayashi, et al., "Hydrogen generation by reaction of Si nanopowder with neutral water," J Nanopart Res, vol. 19, 9 pages, 2017.

Nicolson, et al., "Clinical Effects of Hydrogen Administration: From Animal and Human Diseases to Exercise Medicine," International Journal of Medicine, vol. 7, pp. 32-76, 2016.

Pastore, et al., "Transdermal patches: history, development and pharmacology," British Journal of Pharmacology, vol. 172, pp. 2179-2209, 2015.

Pereira, et al., "Traditional Therapies for Skin Wound Healing," Advances in Wound Care, vol. 5. No. 5, pp. 208-229, 2016.

Shields, et al., "Still too hot: Examination of water temperature and water heater characteristics 24 years after manufacturers adopt voluntary temperature setting," J Burn Care Res. 2013; 34(2): 281-287.

Tamaki, et al., "Hydrogen-Rich Water Intake Accelerates Oral Palatal Wound Healing via Activation of the Nrf2/Antioxidant Defense Pathways in a Rat Model," Oxidative Medicine and Cellular Longevity, vol. 2016, 13 page, 2016.

* cited by examiner

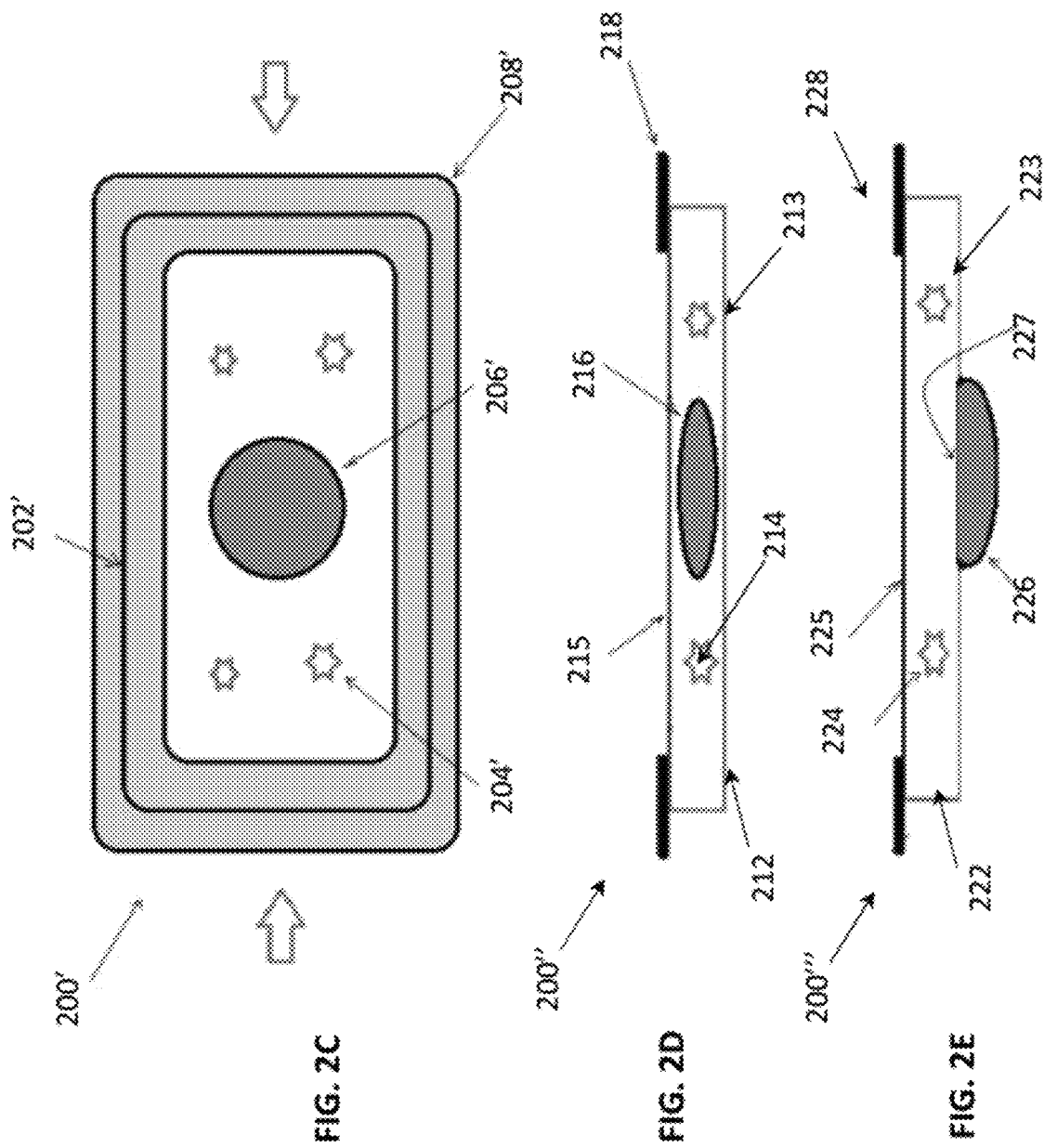

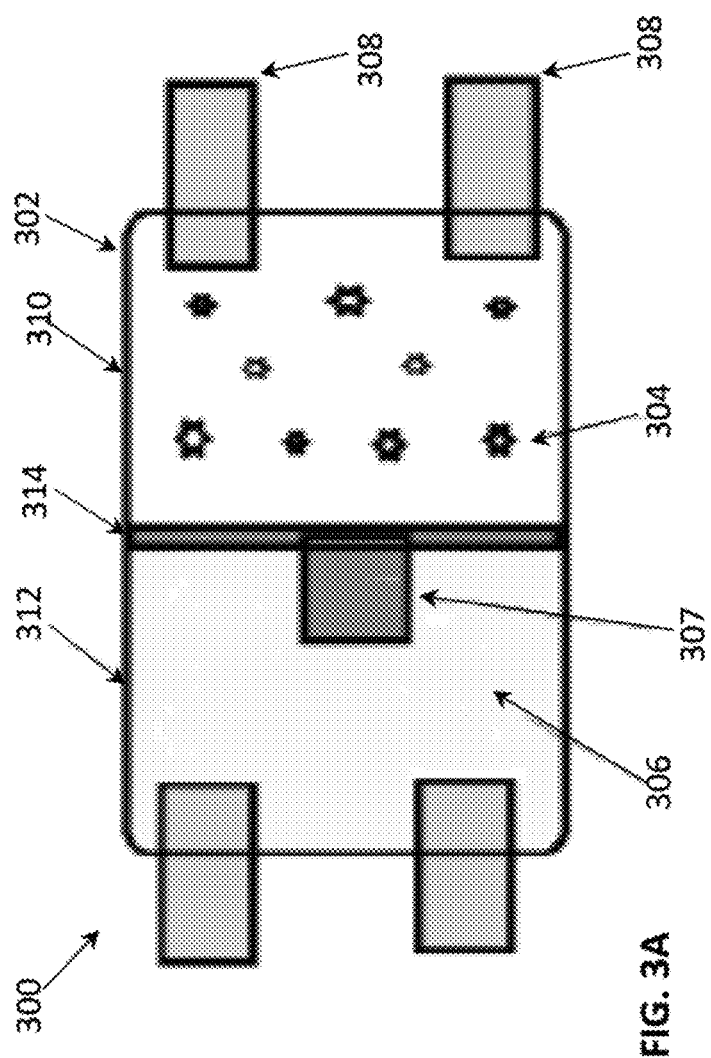
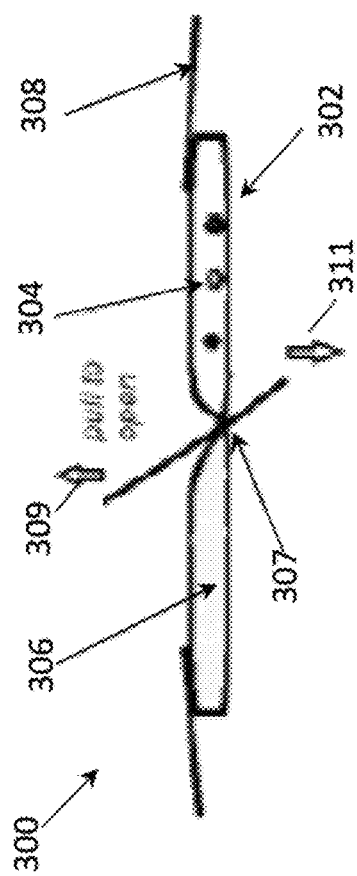
FIG. 3A
FIG. 3B

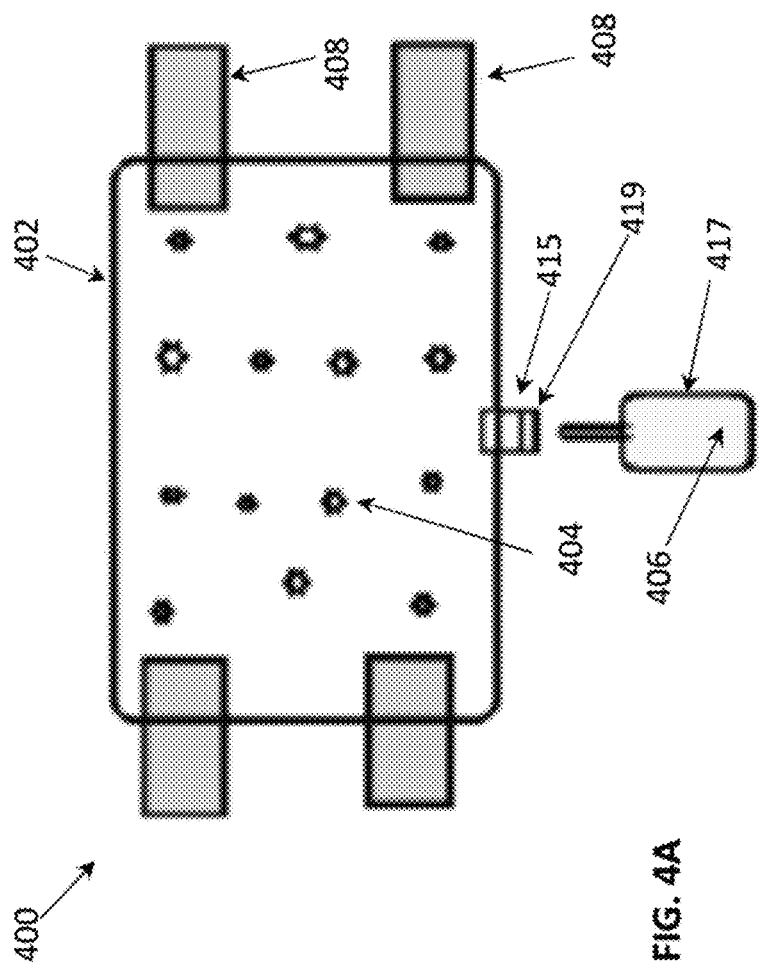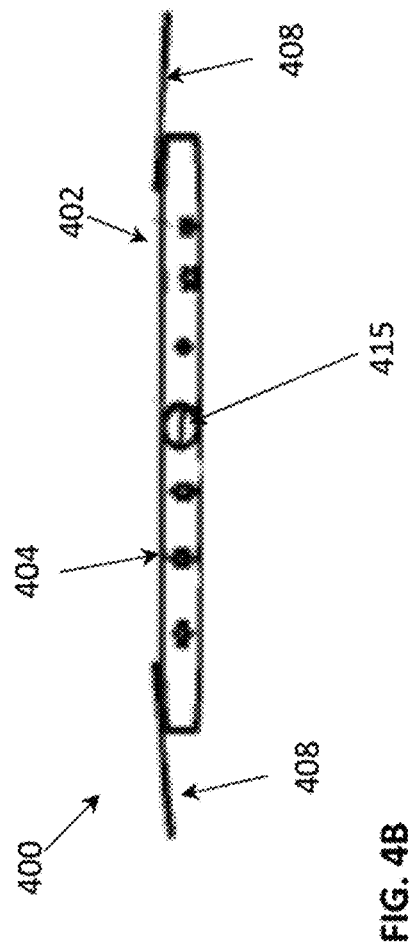
FIG. 4A
FIG. 4B

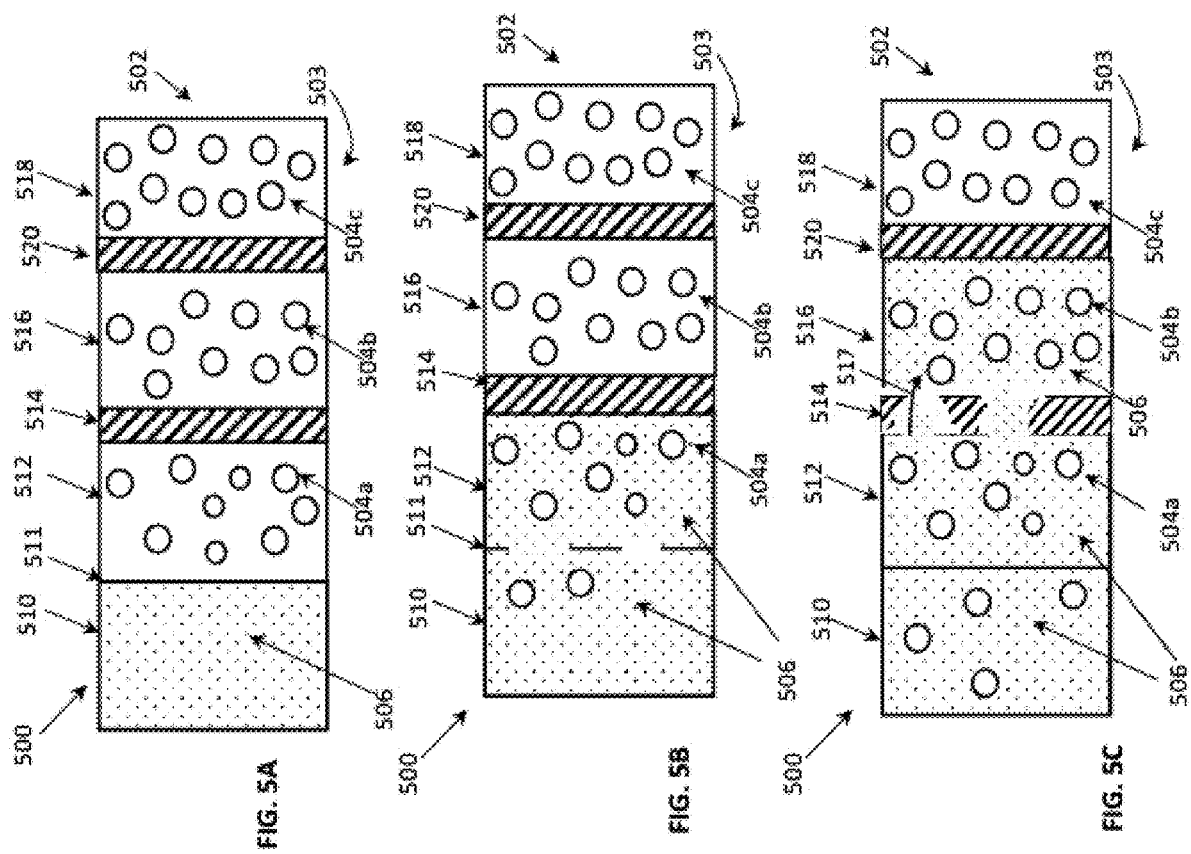

SYSTEMS AND METHODS FOR TOPICAL APPLICATION OF MOLECULAR HYDROGEN

TECHNICAL FIELD

The present disclosure relates to a hydrogen generating and delivering system for external application of molecular hydrogen to a target area of the subject's skin to provide a therapeutic effect.

BACKGROUND

Hydrogen therapy includes the use of molecular hydrogen ($H_2$) for treatment and prevention of various conditions and diseases. Basic and clinical research has revealed that hydrogen is an important physiological regulatory factor with antioxidant, anti-inflammatory and anti-apoptotic protective effects on cells and organs. See Huang et al., Recent advances in hydrogen research as a therapeutic medical gas, Free Radical Res. 44(9) (2010): 971-82; Ohta, Recent progress toward hydrogen medicine: potential of molecular hydrogen for preventive and therapeutic applications. Curr Pharm Des. 17(22) (2011): 2241-52. Prominent effects of the $H_2$ treatment were documented for many oxidative stress-related diseases, and hydrogen-based therapy is a rapidly growing area.

Existing methods for delivering of molecular hydrogen to a patient's body include administration of $H_2$ inhalations, oral administration of hydrogen-infused liquids (e.g., $H_2$-enriched water) or hydrogen-releasing solids (e.g., capsules or tablets), injecting $H_2$-containing solutions, and other ways of delivering hydrogen to the subject's body. Topical delivery of hydrogen has been also gaining interest, particularly for alleviation of various skin conditions and in the anti-ageing cosmetics industry. However, existing techniques for external application of hydrogen on body surfaces have certain disadvantages, including direct contact between the skin and hydrogen-generating chemicals, difficulty in achieving a targeted $H_2$ delivery, and somewhat cumbersome designs of application systems.

Accordingly, there is a need for improved techniques for external delivery of molecular hydrogen to a subject's skin as part of a hydrogen therapy.

SUMMARY OF THE INVENTION

Accordingly, in various aspects, systems, devices, and methods for delivery of molecular hydrogen to the subject's skin are provided. A hydrogen-delivering system includes a housing having at least one compartment including chemical compounds that are disposed within the housing such that they enter into a reaction to generate hydrogen gas upon activation of the system. The hydrogen-delivering system is configured to be removably attached to the surface of the subject's skin, and hydrogen generated within the housing upon the activation action is diffused from within the housing, through its wall, to the target surface of the subject's body. The system can thus deliver the hydrogen to the specific area of the subject's skin for a certain period of time, thereby providing a therapeutic effect in a safe and easy-to-use manner. The hydrogen-delivering system can be configured to be self-administered by the subject, and the system can be disposable.

The hydrogen-delivering system in accordance with embodiments of the present disclosure can have various configurations and sizes that allow administration of molecular hydrogen to various areas of the subject's body. For example, in some embodiments, the housing has a size that allows positioning it over a relatively small and flat surface of skin. In some embodiments, however, the housing can be configured to fit over a curved surface, such as a surface of a joint. The hydrogen-delivering system can have suitable attachment elements that allow affixing the housing to a surface of the skin for a targeted delivery of hydrogen.

In one aspect, a hydrogen-generating system for external use is provided that includes a housing and at least one attachment element configured to attach the housing to a surface of the subject's skin when the housing is positioned against the surface of the skin. The housing can include a first portion comprising at least one dry chemical, and a second portion, separate from the first portion and comprising a liquid (e.g., aqueous) composition configured to react with the at least one dry chemical to generate molecular hydrogen. The housing has a first, skin-facing and skin-contacting surface configured to be positioned adjacent to the subject's skin, the first surface being at least partially hydrogen-permeable and impermeable to the dry chemical(s) and the liquid composition. The system is configured to be activated to cause the liquid composition come in contact and react with the at least one dry chemical to thereby cause generation of the molecular hydrogen that passes through the first surface and is delivered to the subject's skin.

In another aspect, a method of topical application of molecular hydrogen is provided that in some embodiments includes applying a hydrogen-delivering system to a target area of a subject's skin by positioning a skin-facing surface of a housing of the hydrogen-delivering system onto the target area, the housing having enclosed therein a first portion comprising at least one dry chemical and a second portion, separate from the first portion and comprising a liquid composition that is configured to interact with the at least one dry chemical to generate molecular hydrogen. The method further includes causing the liquid composition to at least partially contact the at least one dry chemical within the housing and thereby generate the molecular hydrogen, wherein the generated molecular hydrogen penetrates through at least a portion of the skin-facing surface and is thereby delivered to the target area of the subject's skin.

In another aspect, a hydrogen-generating system for external use is provided that includes a housing having at least one dry chemical and an inlet, wherein the housing has a first surface configured to be positioned onto a target area of a subject's skin, wherein at least a portion of the first surface is hydrogen-permeable. The housing is configured to receive a liquid composition through the inlet thereby the liquid composition contacts the at least one dry chemical which causes generation of molecular hydrogen, wherein the molecular hydrogen passes through at least the hydrogen-permeable portion of the first surface and is delivered to the subject's body through the target area of the subject's skin.

BRIEF DESCRIPTION OF THE DRAWINGS

Non-limiting embodiments of the present invention will be described by way of example with reference to the accompanying figures, which are schematic and are not intended to be drawn to scale. The drawings illustrate exemplary embodiments of the invention and do not therefore limit its scope. In the figures, each identical or nearly identical component illustrated is typically represented by a single numeral. For purposes of clarity, not every component is labeled in every figure, nor is every component of each embodiment of the present disclosure shown where illustration is not necessary to allow those of ordinary skill in the art to understand the present disclosure. In the figures:

FIG. 2C is a cross-sectional, partially transparent top view of an example of a hydrogen-delivering system in accordance with some embodiments;

FIG. 2D is a cross-sectional, partially transparent side view of an embodiment of the hydrogen-delivering system of FIG. 2C;

FIG. 2E is a cross-sectional, partially transparent side view of another embodiment of the hydrogen-delivering system of FIG. 2C;

FIG. 3A is a cross-sectional, partially transparent top view of an example of a hydrogen-delivering system in accordance with some embodiments;

FIG. 3B is a cross-sectional, partially transparent side view of the hydrogen-delivering system of FIG. 3A;

FIG. 4A is a cross-sectional, partially transparent top view of an example of a hydrogen-delivering system in accordance with some embodiments;

FIG. 4B is a cross-sectional, partially transparent side view of the hydrogen-delivering system of FIG. 4A;

FIG. 5A is a cross-sectional, partially transparent side view of an example of a hydrogen-delivering system in accordance with some embodiments;

FIG. 5B is a cross-sectional, partially transparent side view of the hydrogen-delivering system of FIG. 5A, illustrating contents of first and second compartments of a system's housing being at least partially mixed, wherein the mixing results in molecular hydrogen being generated; and FIG. 5C is a cross-sectional, partially transparent side view of the hydrogen-delivering system of FIG. 5A, illustrating contents of first, second, and third compartments of the system's housing being at least partially mixed, wherein the mixing results in molecular hydrogen being generated.

DETAILED DESCRIPTION

Figure 1A:
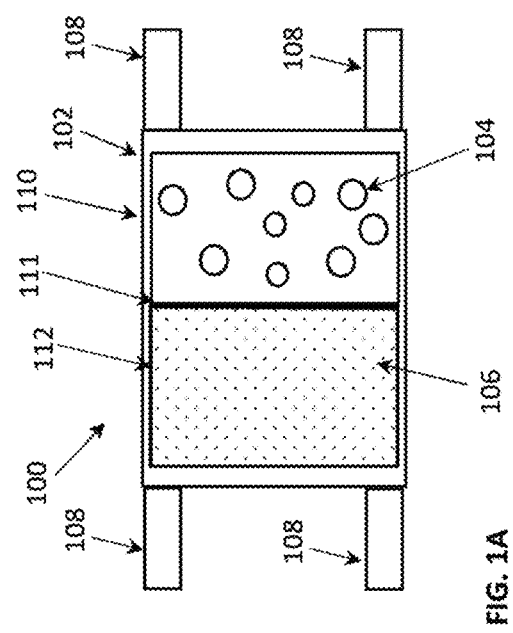
FIG. 1A is a cross-sectional, partially transparent top view of an example of a hydrogen-delivering system in accordance with some embodiments.

The present disclosure provides a hydrogen-delivering system for external administration of molecular hydrogen ($H_2$) to the subject's skin, and methods for delivering topical hydrogen therapy. The molecular hydrogen is generated within the interior of a housing of the hydrogen-delivering system in a safe manner, and the hydrogen can be administered to a target area on the subject's skin for a duration of time that is sufficient to deliver a therapeutic effect.

Molecular hydrogen is a known antioxidant that is also capable of providing anti-inflammation effect, and the hydrogen gas can thus be administered as a therapy for treatment and/or prevention of a variety of diseases. Topical administration of molecular hydrogen, albeit less common than other ways of delivering hydrogen, has recently been gaining attention from the drugs and cosmetics industries. However, as mentioned above, existing approaches of topical hydrogen application have certain shortcomings. For example, patent application No. US 2013/0323190 describes an external use composition that includes fine particles of metal or metal alloy storing hydrogen (such as magnesium hydride) that are in direct contact with the skin, which may cause undesirable effects on the skin, such as irritation, redness, burning and rash. Moreover, magnesium hydride, which is a hazardous material, can get into the subject's mouth and also reach respiratory tract. Patent application No. US 2018/0092816 describes topical hydrogen-containing skin care products that are in direct contact with the skin. Sodium borohydride is proposed as a hydrogen generator, which can cause allergic reactions during direct skin contact.

In embodiments of the present disclosure, chemical compounds enclosed within a housing (e.g., a sealed enclosure) of the hydrogen-delivering system and capable of generating molecular hydrogen are disposed separately from the subject's skin, such that the compounds remain separated from the skin during hydrogen release at least through a skin-facing surface of the housing. Thus, the system delivers hydrogen without any detrimental effects on the skin. Also, the hydrogen is generated only as required, upon a certain action performed with respect to the housing and/or its features. In this way, the hydrogen is administered to a desired target area, at a desired time, and for a certain duration time that is sufficient to provide a therapeutic effect. The chemical compounds include dry compounds and liquid compounds that are mixed only once the system is activated. Before the activation, the hydrogen-delivering system can be safely transported and stored. Moreover, the hydrogen-delivering system is self-contained and it can be made suitable for self-administration, such that it can be used outside a clinical setting.

The hydrogen-delivering system or device in accordance with the present disclosure can have various configurations. For example, the hydrogen-delivering system can have a housing having one or more compartments and the housing can be configured to be placed against the surface of the subject's skin. The housing can be a pad, patch, bag, pouch, bandage, compress, band, tape, mask or any other type of a topical applicator container configured to enclose therein one or more chemical compounds capable of generating molecular hydrogen upon activation of the housing. In some embodiments, the chemical compounds include an aqueous composition that is separated from other, dry chemical compound(s) until the system's activation. The chemical compounds are selected such that they react in a safe way, without generating excess of hydrogen (which may cause explosion in extreme circumstances). Also, when more than one dry chemical is used, they do not react until the dry chemicals are mixed with the aqueous composition.

Non-liming examples of the aqueous composition include a water suspension of calcium hydroxide, a water solution of sodium chloride and copper (II) sulfate, water, a suitable acid, base, and other suitable solutions. Non-liming examples of the dry compounds include electrochemical series, e.g., aluminum, magnesium, zinc, iron; and compounds such as, e.g., magnesium hydride, calcium hydride, and other suitable dry compounds where hydrogen is stored and is released once in contact with a liquid (e.g., water or another liquid) solution, or their mixture(s). Molecular hydrogen can be produced from a suitable chemical reaction, or it can be released from molecular storage. In some embodiments, the hydrogen generating or releasing reaction can also generate a certain amount of heat, which can have a therapeutic effect. In embodiments, components used to produce hydrogen are safe and, in some embodiments, Generally Recognized As Safe (GRAS)-certified. In some embodiments in which magnesium and/or magnesium hydride are used, these compounds are not in a form of powder, since they can be explosive in such form. An additional substance can be added, e.g., magnesium hydromagnesite, to avoid the danger of explosion.

In some embodiments, at least one side of the housing, such as the skin-facing surface, can be configured to be placed adjacent to the skin. For example, at least the skin-facing surface of the housing or, in some implementations, the entire housing (or portion(s) thereof), can be configured so as to conform to the surface of the skin. For example, if the hydrogen-delivering system is configured to deliver hydrogen to a relatively flat, small area of the skin, the housing can be relatively flat and it can have the size appropriate for a target area. If the hydrogen-delivering system is configured to deliver hydrogen to a subject's knee, finger, elbow, or another curved surface (e.g., a subject's face), at least a portion of the housing can be shaped and sized to conform to that curved surface. The hydrogen-delivering system can be configured for delivering hydrogen treatment to the shoulder, ankle, head, face, abdominal area and any other area of a subject's body. The configuration of the system can also depend on the condition which the system is intended to prevent and/or treat and on the way in which the hydrogen is to be administered. For example, if a relatively quick application of a small amount of hydrogen is required, the housing can be thinner and have a smaller hydrogen-releasing surface area as compared to a housing of a system that is made for a more prolonged administration of larger amounts of $H_2$. Other features of the system such as, e.g., the attachment element(s), the way in which the system is activated, can also vary depending on characteristics of the targeted area, therapeutic application, and other factors.

The hydrogen-delivering system can include any type of attachment elements configured to attach the housing to the surface of the skin. The attachment elements, which can be coupled to or integrally formed with the housing, can be, for example, adhesive elements (e.g., a tape, bandage, etc.). In some implementations, for example, when the hydrogen-delivery system is for application to the knee, elbow, ankle, or wrist (or any other joint), the attachment elements can have a buckle, clasp, or another fastening element such that the opposed ends of the attachment elements are coupled to one another. Any other type and number of attachment elements can be used, depending on the target area of the application of the hydrogen-delivering system. Furthermore, in some embodiments, the skin-facing surface of the housing can be at least partially adhesive. Thus, in some implementations, one or more portions of the housing (e.g., its skin-facing surface or a portion thereof, such as its edges along the perimeter) form the attachment element(s).

The housing of the hydrogen-delivering system can be formed from various suitable materials, non-limiting examples of which include polyethylene, polypropylene, nanomaterials, biopolymers, and/or other materials or combinations thereof. More than one material can be used to make the housing. In some embodiments, the skin-facing surface can be made from one type of material(s), whereas the opposite side (with its outer surface facing away from the skin) can be made from another type of material(s). The skin-facing surface can be made from a hydrogen-permeating material, such as, e.g., low density polyethylene (LDPE), and the opposite side (and side surfaces, in some implementations) can be made from a material that is less permeable or not permeable to molecular hydrogen such as, e.g., high density polyethylene (HDPE). In some embodiments, the skin-facing surface of the housing can be made in the form of a porous membrane having pores of a size that allows a certain rate of $H_2$ permeation through the membrane. In some embodiments, the porous membrane or another type of the skin-facing surface can be made such that only portions of it are permeable to hydrogen, to deliver the hydrogen in a targeted manner. For example, if the housing is in the form of a face mask, only certain portions of the mask can be permeable to hydrogen to administer hydrogen to specific areas of the face. Also, such implementations can be used if the hydrogen-delivering system is made to deliver hydrogen in combination (either simultaneously or not) with one or more therapeutic agents such as, e.g., analgesics, antiseptics, anti-inflammatory drugs, plant-based compounds, etc. As an example, the hydrogen-delivering system can deliver both hydrogen and at least one therapeutic agent (e.g., a corticosteroid, vitamin or a vitamin-derivative, an herbal compound, etc.) for alleviating symptoms of psoriasis, burns, insect bites, etc. In embodiments in which the hydrogen-delivering system additionally delivers at least one therapeutic agent, the skin-facing surface of the housing can have an area that, in addition to or instead of hydrogen, allows the therapeutic agent to be released therefrom. The therapeutic agent can pass through the skin-facing surface or, in some embodiments, a part of the skin-facing surface can be removable to allow, e.g., a compartment storing the therapeutic agent become exposed such that the therapeutic agent can be applied to the skin. Other modifications can be implemented additionally or alternatively.

The skin-facing surface can be made such that it is soft, flexible, and not irritating to the skin, to ensure patient's comfort during delivery of the $H_2$ therapy. For example, in some embodiments, the skin-facing surface can be made from a suitable plastic material or a combination of materials. In some embodiments, additionally or alternatively, the skin-facing surface can be formed of a fabric material that is not permeable to water and chemical reagents, but that allows hydrogen to penetrate therethrough.

Regardless of its specific properties, the skin-facing surface of the housing, which can also be referred to as a skin-contacting surface (it is positioned in close contact with the skin), is permeable to molecular hydrogen and not permeable to the chemicals, including the aqueous composition, enclosed within the interior or inner cavity of the housing. In this way, as mentioned above, these chemicals do not contact the subject's skin at any point during or after the delivery of the $H_2$ therapy.

Regardless of the specific configuration and materials of the housing of the system in accordance with the present disclosure, the dry and liquid hydrogen-generating chemicals are disposed within the housing and do not directly contact the subject's skin either before, during, or after generation of hydrogen within the housing. In some embodiments, the skin-facing surface of the housing can include an additional protective layer configured to be positioned over the skin. For example, in some embodiments, the skin-facing surface of the housing can include one or more layers generated in accordance with 3M™ Cavilon™ technology, though any other technology can be used additionally or alternatively. The skin-facing surface can be formed so as to provide an improved contact with the skin, while being permeable to molecular hydrogen.

The hydrogen-delivering system in accordance with embodiments of the present disclosure is activated for hydrogen delivery to deliver a therapeutic effect. This involves bringing a liquid composition into contact with the dry reagents, which leads to a chemical reaction that releases molecular hydrogen. In some embodiments, one or more dry chemical compounds enclosed in the housing of the hydrogen-delivering system are hydrogen-storage compounds that release the stored hydrogen upon contact with a liquid (e.g., aqueous) composition. The hydrogen-storage compounds can be, for example, complex organic polymers that are filled with molecular hydrogen. When interacting with a solution (e.g., a water solution), hydrogen escapes from its storage. For example, in some embodiments, compounds available from Dibal LLC (San Diego, CA) can be used. The system is applied to the target site on the subject's body before or after the system is activated to generate molecular hydrogen. The chemical reaction or substance(s) with hydrogen storage in the enclosed housing of the hydrogen-delivering system produces molecular hydrogen. The thus generated molecular hydrogen gas diffuses at least through the skin-facing surface of the housing and can penetrate into the subject's body through the skin to deliver a therapeutic effect to the skin and underlying tissues.

In some embodiments, the housing can be made from two portions or layers of a plastic film that are joined together at the edges. The layers can be made from the same or different materials. For example, in some embodiments, as discussed above, the skin-facing layer that is configured to be positioned adjacent to the skin (the layer contacts the skin) can be made from a material that is permeable to hydrogen, whereas the opposite side of the housing can be made from a material that is less permeable or not permeable to hydrogen (e.g., a thick plastic film). In this way, the hydrogen is delivered to the skin in a more targeted manner, with decreased loss of hydrogen. In addition, the amount of hydrogen released into the atmosphere is decreased.

In some implementations, portions of the housing other than the skin-facing surface (in addition to the skin-facing surface) can be configured to allow molecular hydrogen pass therethrough from the interior of the housing and towards the subject's skin. For example, for some applications, it can be beneficial to allow hydrogen be released from one or more sides of the housing of the hydrogen-delivering system.

Figure 1B:
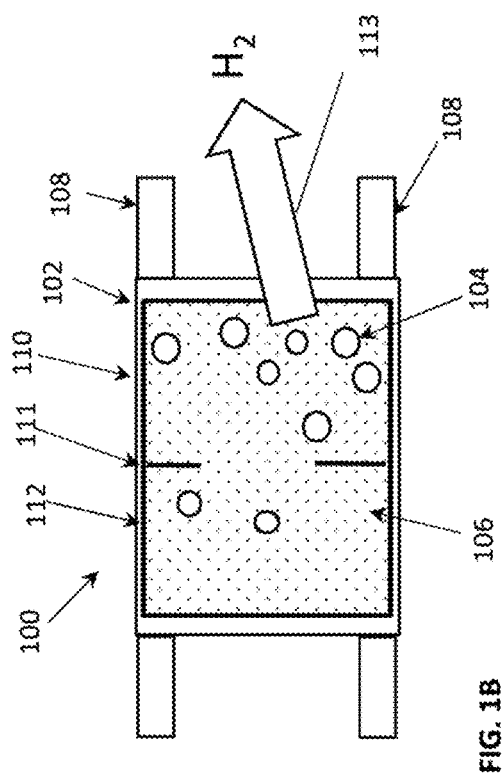
FIG. 1B is a cross-sectional, partially transparent side view of the hydrogen-delivering system of FIG. 1A, illustrating a divider between compartments of a housing of the system in at least partially removed state.

FIGS. 1A and 1B illustrate an embodiment of an example of a hydrogen-delivering system 100 in accordance with the present disclosure. As shown in FIG. 1A, the system 100 includes a housing 102 that includes a first portion comprising at least one dry chemical 104 and a second portion, separate from the first portion and comprising a liquid composition 106 configured to react with the at least one dry chemical 104 (which is a hydrogen-generating and/or hydrogen-storing agent) to generate molecular hydrogen. In this example, the housing 102 includes a first compartment 110 having the dry chemical 104 and a second compartment 112, separate from the first compartment 110, that includes the liquid composition 106. The dry chemical 104 can be in the form of particles of a suitable size and shape, and the liquid composition 106 can be in the liquid form, as shown schematically in FIG. 1A. The housing 100 has a skin-facing surface having at least a portion thereof that is permeable to $H_2$ but not permeable to the dry chemical 104, the liquid composition 106, and product(s) of the chemical reaction therebetween, besides $H_2$.

The system 100 can include a plurality of attachment elements 108 configured to attach the housing 102 to a surface of the subject's skin when the housing 102 is positioned over a target area of the subject's skin, with its skin-facing surface positioned over the target area. Four attachment elements 108, which can be adhesive elements or elements of any other type, are shown by way of example only, as any other number of the attachment elements can be used, including one, two, three or more than four. The attachment elements 108 are shown to have a certain size by way of example only as well. For example, in some implementations, instead of two attachment elements on each of the shorter sides of the housing 102, one attachment element can be formed on each shorter sides, and a width of such attachment element can be substantially equal to a length of the housing's shorter side. As another variation, one or more attachment elements can be formed on the longer side of the housing 102, or the attachment elements can be formed on more than two sides of the housing. The attachment elements can be formed in any other manner. For example, in some embodiments, the attachment element(s) are formed around the entire housing, or around a portion of the housing. Also, in some implementations, the housing can be configured to be attached to a subject's body using a bandage, elastic band, or any other one or more attachment features.

In some embodiments, the housing 102 itself may have one or more portions that can function as attachment elements. For example, one or more areas of the skin-facing surface of the housing 102 can be adhesive such that the skin-facing surface is disposed in close contact with the skin. For example, in some cases, an area of the skin-facing surface along a perimeter of the skin-facing surface can be adhesive such that this area is used to adhere the housing to the subject's skin, whereas the inner area of the skin-facing surface is configured to let molecular hydrogen pass therethrough when the system is being used. This allows to deliver hydrogen to the skin in the targeted manner, and such that loss of hydrogen is minimized.

The first and second compartments 110, 112 are separated from one another by a divider member or divider 111 in a non-activated state of the system 100, as shown in FIG. 1A. The divider 111 can be formed between the first and second compartments 110, 112 such that it can be at least partially broken, removed, or otherwise changed upon a certain action. Thus, FIG. 1B shows the divider 111 being partially removed such that the contents of the first and second compartments 110, 112 (the dry chemical 104 and the liquid composition 106, respectively) are mixed thereby generating molecular hydrogen that passes through the outer wall of the housing 102 (e.g., the skin-facing surface) and is released, as shown schematically by an arrow 213 in FIG. 1B. Other reactants that remain after the dry chemical(s) 104 reacts with the liquid composition 106 remain within the housing 102 that is configured to keep its content, other than generated molecular hydrogen, enclosed therein.

The released hydrogen is transferred into the target area of the skin and it diffuses into the underlying tissues of the subject's body. The hydrogen can continue being delivered to the target area for a certain period of time, selected to be sufficient to provide a therapeutic effect. The period of time can be, for example, from about 1 minute to about two hours, from about 1 minute to about one hour, from about 1 minute to about 30 minutes, from about 1 minute to about 20 minutes, from about 1 minute to about 10 minutes, from about 10 minutes to about 30 minutes. In some embodiments, the period of time can be from about 30 minutes to about 2 hours. In some embodiments, the period of time can be from about 1 hour to about 8 hours, or from about 1 hour to about 6 hours, or from about 2 hours to about 8 hours, or from about 2 hours to about 6 hours. The period of time can depend on a size, shape, and other properties of the hydrogen-delivering system, type of treatment, the area being treated, and other factors. The hydrogen-delivering system can be configured to release hydrogen for a predetermined duration of time. In the course of the therapy, multiple systems, such as the hydrogen-delivering system 100 or any other hydrogen-delivering system in accordance with the present disclosure, can be applied to a target area. For example, the therapy can involve application of the same or different hydrogen-delivering systems to the target area over a period of a day, several days, a week, several weeks or any other period of time.

After the delivery of the hydrogen is completed, the system 100 can be removed from the target area. The system 100 can be disposable.

In the example of FIGS. 1A and 1B, the system 100 can be activated to release hydrogen in a number of different ways. For example, pressure can be applied over the housing 102, or the housing 102 can be subjected to another manipulation, depending on its configurations and configurations of the compartments in its inner cavity. In some implementations, as discussed in more detail below, the divider 111 can include or can be coupled to a feature that is referred to herein as an activation feature that is configured to be manipulated to cause the divider 111 to change the divider configuration. The activation feature can be a tag, a tab, a button (e.g., a press or push button), or another feature that can be manipulated (e.g., pulled, pushed, pressed, removed, etc.) to thereby remove the divider between compartments within the housing 102.

It should be appreciated that the first and second compartments 110, 112 are shown in FIGS. 1A and 1B as separated along a longer side of the generally rectangular housing 102 by way of example only. In some embodiments, the first and second compartments 110, 112 can be separated along a thickness of the housing 102 or in another manner. It should also be appreciated that the housing 102 of FIGS. 1A and 1B is shown as a generally rectangular enclosure by way of example only. The housing can be any one of various other shapes, including regular (e.g., square, oval, round, etc.) and irregular shapes.

The aqueous composition can be separated from the dry chemical compounds inside a housing of the hydrogen-delivering system in various ways. In some embodiments, the aqueous composition is encapsulated within a plurality of capsules that each releasably carry a small amount of a liquid composition. The capsules and the dry chemical compounds can be intermingled within the interior cavity of the housing, and the capsules are configured to release the aqueous composition upon application of pressure exerted upon the housing.

Figure 2A:
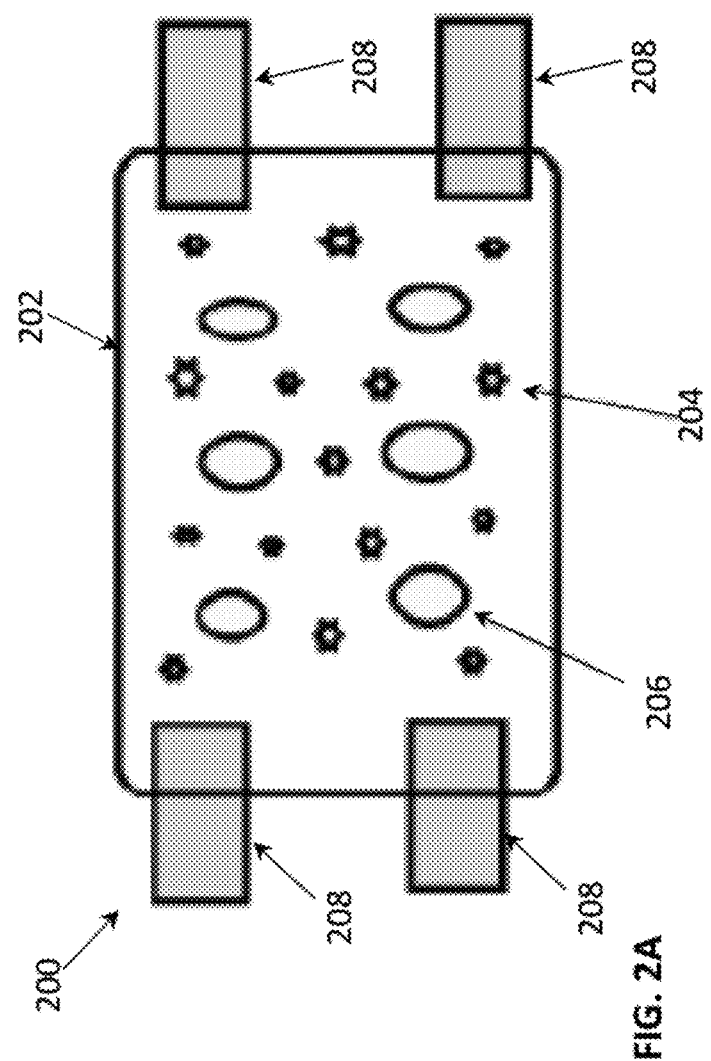
FIG. 2A is a cross-sectional, partially transparent top view of an example of a hydrogen-delivering system in accordance with some embodiments.
Figure 2B:
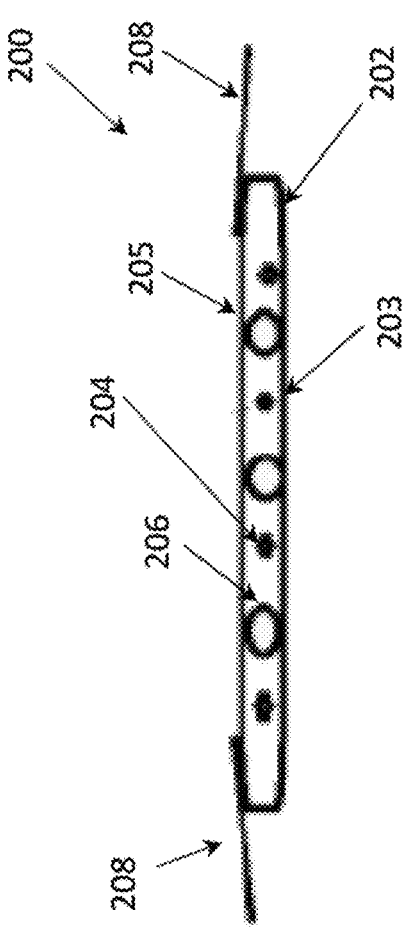
FIG. 2B is a cross-sectional, partially transparent side view of the hydrogen-delivering system of FIG. 2A.

FIGS. 2A and 2B illustrate an embodiment of an example of a hydrogen-delivering system 200. As shown in FIG. 2A, the system 200 includes an enclosed housing 202 including at least one first compound 204 (e.g., dry chemicals) and at least one second compound 206 in the form of a plurality of pressure-dependent capsules releasably carrying a liquid solution (e.g., an aqueous composition). The capsules can be formed from any suitable water-resistant or water-impermeable material, such as one or more plastic materials. The capsules are formed such that they can break and release their content. In some embodiments, the pressure-dependent capsules can be made of a frangible plastic material, for example, cellophane. The volume of the capsules may depend on how much aqueous solution is required for reaction. For example, in some embodiments, the capsules can be from about 1 mm to about 3 mm in diameter in their largest dimension. It should be appreciated however that the capsules can have any other size.

The system 200 also includes a plurality of attachment elements 208 coupled to the housing 202 and configured to be releasably coupled to the subject's skin to thereby position the housing 202 in close contact with the skin. In this embodiment, the first compound 204 can be in the form of pellets, bullets, balls, granules, tablets, powder or otherwise-shaped small particles made of one or more dry chemicals. The particles can have one or more layers, including concentric or otherwise formed layers. The particles can be enclosed within gauze, porous paper, or another material.

In FIGS. 2A and 2B, the first compound 204 is shown in the form of star-shaped particles of varied sizes for the illustration purposes only, as the first compound 204 can have any other shapes, including different or the same shapes within the same housing 202. The plurality of capsules 206 can also have various configurations, shapes, and sizes.

Regardless of its specific shape(s) and size(s), in this example, the first compound 204 is interspersed with the plurality of capsules 206 having an aqueous composition releasably enclosed therein. As shown schematically in FIG. 2B, in this embodiment, the first compound 204 and the capsules 206 can form one layer, though in other embodiments the housing 202 can include more than one layer of the first compound 204 and the capsules 206. Also, the first compound 204 and the capsules 206 can form other arrangements within the housing, including arrangements different from layers.

It should be appreciated that the housing 202 of a rectangular shape is shown in FIGS. 2A and 2B by way of example only, as the housing 202 can have other suitable shapes, including round, oval, or any other regular or irregular shapes. A skin-facing surface 203 and an opposite surface 205 (shown in FIG. 2B) can be formed from different materials, and at least a portion of the skin-facing surface 203 is hydrogen-permeable and not permeable to the first and second compounds 204, 206. In this way, there are no leaks or other inconveniences to the subject. The system 200 can be disposable and it can be discarded after use.

The attachment elements 208 can have various configurations. In this example, four attachment elements 208 formed on opposite sides of the shorter sides of the housing 202 are shown by way of example only, as other number of attachment elements can be used. The attachment element 208 can be in the form of an adhesive tape or another adhesive element configured to be releasably attached to the skin, and they can have various shapes and sizes.

In the embodiment of FIGS. 2A and 2B, to activate the chemical reaction between the first and second compounds 204, 206, pressure can be applied to the housing 202 to thereby cause the aqueous composition be released from the capsules 206. The system 200 can be configured such that pressure can be applied to the housing 202 before the system 200 is affixed to the skin, or after the system 200 has been positioned in close contact with and coupled to the skin using the attachment elements 208. Once the capsules 206 are broken under the action of the pressure (applied, e.g., over the upper surface 205 (FIG. 2B), and start releasing the liquid composition, the liquid composition contacts the first compound 204 and molecular hydrogen is released as a result of the hydrogen-generating reaction. The pressure can be applied before the system 200 is attached to the target area of the skin. In some embodiments, alternatively, the pressure can be applied onto the housing after the system 200 is attached to the target area of the skin. The generated molecular hydrogen passes through a wall of the housing 202 and is thus delivered to the skin.

In some embodiments, the housing can include more than one compartment such that the interior of the housing can be divided into separate portions (two or more). The portions can include respective chemical compounds that are thus disposed separately from one another within the housing, i.e., disposed in separate compartments. The dividers, such as common walls or other types of dividers, between the two or more compartments within the housing can be at least partially broken or otherwise removed to allow contents of the compartments to mix and thereby generate $H_2$.

In embodiments described above, a second component is shown in the form of at least one capsule, and the examples of FIGS. 2A, and 2B show second components in the form of multiple capsules having enclosed therein a liquid composition. In some embodiments, however, a second component carrying a liquid composition can be in the form of a single element such as, e.g., a capsule or another type of enclosure, which in some cases may be pressure dependent. In some implementations, the single capsule (or another type of an enclosure for a liquid) may be larger than in embodiments with more than one capsule. Also, the capsule can be positioned in the system such that a user can conveniently manipulate the system (e.g., by directly or directly manipulating the capsule) to cause the capsule to release its content into within the housing with the dry components. For example, the capsule can be positioned such that it is conveniently accessible to the user, and the user can thus manipulate (e.g., press) the capsule to cause it to release the liquid composition. In some embodiments, the system is configured to be self-administered.

FIG. 2C illustrates an example of a hydrogen-delivery system 200' in accordance with embodiments of the present disclosure. As shown, the system 200' includes an enclosed housing 202' including at least one first component 204' (e.g., dry chemicals) and a second compound 206' in the form of a single pressure-dependent capsule releasably carrying a liquid solution (e.g., an aqueous composition). In this embodiment, an attachment element 208' of the system 200' is formed around the entire perimeter of the housing 202'. For example, the attachment element 208' can be in the form of an adhesive strip formed on the skin-facing side of the housing 202'.

The capsule can be formed from any suitable water-resistant or water-impermeable material, such as one or more plastic materials. The capsule is formed such that it can break and release their content. In some embodiments, the pressure-dependent capsule can be made of a frangible plastic material, for example, cellophane. The volume of the capsules may depend on how much aqueous solution is required for reaction and on other factors, such that the size and shape of the housing. For example, in some embodiments, the capsules can be from about 0.5 mm to about 5 cm, from about 1 mm to about 5 cm, or from about 10 mm to about 5 cm in diameter in their largest dimension. It should be appreciated however that the capsules can have any other size. In some embodiments, a volume of a liquid composition (e.g., aqueous solution) encompassed within a single capsule can be between about 1.5 ml and about 4 ml. The capsule can include other volumes of a liquid composition.

A single capsule including a liquid composition such as, e.g., the capsule 206' shown included in the system 200', can be disposed differently with respect to the housing. For example, in some embodiments, the single capsule can be positioned entirely within the housing. Thus, FIG. 2D illustrates an embodiment of a hydrogen-delivery system 200" that is similar to hydrogen-delivery system 200' (FIG. 2C) and that has a housing 212 having included therein a first component 214 and a second component 216 in the form of a single capsule, and an attachment element 218. The housing 212 has a skin-facing surface 213 and an opposite surface 215, and the capsule 216 is enclosed within the housing 212 in its entirety.

In some embodiments, a capsule can at least partially protrude from a surface of the housing of a hydrogen-delivery system. In this way, the pressure applied to the housing causes the liquid content of the housing be released from the capsule into the interior of the housing. FIG. 2E illustrates an embodiment of a hydrogen-delivery system 200''' that is generally similar to hydrogen-delivery systems 200' (FIG. 2C) and 200'' (FIG. 2D) and that has a housing 222 having included therein a first component 224 and a second component 226 (a single capsule), and an attachment element 228. The housing 222 has a skin-facing surface 223 and an opposite surface 225, and the capsule 226 is at least partially disposed on the skin-facing surface 223 such that the capsule 226 protrudes from the skin-facing surface 223. In this way, the capsule 226 can be accessible to a user. Before activation of the system 200''', the interior of the capsule 226 is separated from the interior of the housing 222 by a portion 227, which can be any type of a divider configured to at least partially break to allow the interior of the capsule 226 communicate with the interior of the housing 222 and thereby release an aqueous solution from inside the housing. For example, applying pressure to the system 200''' can cause the divider portion 227 to break or otherwise change its configuration. Thus, the first component 224 which can be, e.g., in the form of a chemical powder (or in any other form), comes in contact with the liquid composition released from the capsule 226 and becomes wet, upon which a chemical reaction (which can be a slow chemical reaction) begins to release gaseous hydrogen. Hydrogen passes through the skin-facing surface 223 (which can be formed from, e.g., fabric) that is disposed over a targeted area of the subject's skin.

It should be appreciated that the second component 226 in the form of a single capsule is shown in FIG. 2E to be substantially entirely outside of the housing 222 by way of example only. The top surface of the capsule 226 (i.e., in this example, the surface that is adjacent to the housing and that is or includes the portion 227) can be disposed at least partially within the housing 222. Thus, in some implementations, a portion of the capsule 226 extends beyond the housing 222 and a portion of the capsule 226 is within the housing 222. In addition, it should be appreciated that the single capsule is shown in FIGS. 2C-2E by way of example only, as more than one capsule can be disposed within the housing of a hydrogen-delivering system or at least partially outside of the housing.

FIGS. 3A and 3B illustrate an embodiment of an example of a hydrogen-delivering system 300 that includes a housing 302 having first and second compartments 310, 312 separated from one another by a divider member or divider 314. The first compartment 310 includes at least one first compound 304 (e.g., dry chemical compounds), whereas the second compartment 312 includes at least one second compound 306 in the form of an aqueous composition. The interiors of the first and second compartments 310, 312 remain separate from one another (such that the first compound 304 and the aqueous composition 306 do not mix) while the original configuration of the divider 314 is maintained. Similar to hydrogen-delivering system 200 (FIGS. 2A and 2B), the hydrogen-delivering system 300 includes at least one attachment element 308, and four attachment elements are shown by way of example.

As shown in FIG. 3A, the divider member 314 includes or is coupled to an activation feature 307 (e.g., a plastic lock, tab, tag, or another feature) that is configured to be manipulated to thereby cause the divider member 314 at least partially break or otherwise change its original configuration. The change in the configuration of the divider member 314 causes the interiors of the first and second compartments 310, 312 communicate, such that the aqueous composition 306 contacts the first compound 304 such that a chemical reaction between the aqueous composition 306 and the first compound 304 occurs thereby molecular hydrogen is generated and released from the housing 302. In embodiments as shown in FIGS. 3A and 3B, the divider member 314 and the activation feature 307 can have various configurations. In this example, the activation feature 307 includes two parts disposed on opposed sides of the housing 302 and it can be manipulated, e.g., pulled in the opposite directions (as shown by arrows 309, 311 in FIG. 3B) before the system 300 is affixed to the surface of the skin. Pulling the activation feature 307 in the opposite directions away from the housing 302 causes at least a portion of the divider member 314 between the first and second compartments 310, 312 to be removed (e.g., the divider member 314 comes apart) and to thus allow the contents of the first and second compartments 310, 312 to mix.

In some embodiments, the activation feature 307 can be configured such that it can be manipulated to cause the divider member 314 to at least partially break after the system 300 has been attached to the skin. For example, in some implementations, the divider member 314 can be in the zipper-like configuration such that pulling the activation feature 307 causes the "zipper" to open. Any other configuration of the divider member can be substituted. Regardless of the configuration of the divider member and the way in which it is at least partially removed, the contents of the first and second compartments 310, 312 remain within the housing and the integrity of the outer wall of the housing 302 is not preserved.

The housing 302 of the system 300 can have any suitable shape, width, length and thickness, and the substantially rectangular housing is shown in FIGS. 3A and 3B by way of example only. Also, although the housing 302 is shown such that the first and second compartments 310, 312 are separated along a longer side of the rectangular-shaped housing, in other implementations, the first and second compartments 310, 312 can be separated along another side (e.g., thickness) of the housing. For example, a first compartment carrying the dry chemical compounds 304 can be disposed within the bottom portion of the housing (i.e., the portion that will be located closer to the skin when the system is administered onto the subject's skin), whereas a second compartment carrying the aqueous composition 306 can be positioned above the first compartment. In such embodiments, the system can be activated to generate hydrogen by applying pressure thereto. For example, a divider member between the first and second compartments can be configured to be broken upon application of the pressure thereto.

Furthermore, in some embodiments, the housing can include more than one compartment, and some or all of the compartments can have respective different chemical reagents disposed therein such that the reagents are inactive (and safe for transport, storage, and handling) until mixed. The multiple compartments can be configured such that the contents of two or more of them mix, upon the system's activation, substantially simultaneously or in more than one stage. For example, in some implementations, the housing can include more than one activation feature such that a desired spatial and/or temporal delivery of hydrogen is possible. Thus, an activation feature can be manipulated to allow contents of at least two compartments to mix and deliver hydrogen to an area of the subject's skin, and another activation feature can be subsequently manipulated to allow contents of at least two other compartments to mix and deliver hydrogen to an adjacent area of the subject's skin.

In the embodiments shown in FIGS. 1A, 1B, 2A, 2B, 2C, 2D, 2E, 3A, and 3B, the liquid composition can be positioned within the housing during manufacturing of the systems. In some embodiments, the hydrogen-delivering system is configured such that the liquid composition is added to the system's housing with the dry chemicals before the use of the system. The liquid composition can be added to the housing in various ways.

FIGS. 4A and 4B illustrate an embodiment of an example of a hydrogen-delivering system 400 that includes a housing 402 having at least one first compound 404 (e.g., dry chemicals) enclosed therein. In this embodiment, a liquid composition initially is not included in the housing 402, but is rather provided into the interior of the housing 402 via an inlet 415. For example, a container 417 carrying an aqueous composition 406 (shown in FIG. 4A) can be configured to be coupled to the inlet 415 of the housing 402 to thereby deliver the aqueous composition 406 into the interior of the housing 402. The container 417 can be reversibly coupled to the inlet 415 before or after the hydrogen-delivering system 400 is attached to the subject's skin (e.g., using attachment members 408). When delivered into the housing 402, the liquid composition 406 comes in contact with the first compound 404 which causes the first compound 404 to generate molecular hydrogen, which is transmitted from the housing 402 to the subject's skin.

The container 417 can have various configurations. For example, in some embodiments, the container 417 is a compressible bottle, flask, etc., though it should be appreciated that the container 417 can have any other configuration. The container 417 can be coupled to the housing 402, and, after the solution 406 has been delivered inside the housing 402, the container 417 can be removed and the opening of the inlet 415 can be sealed using, e.g., a sealing element 419 schematically shown in FIG. 4A. In some embodiments, the container 417 is included in the system 400 as part of a kit.

The hydrogen-delivering system in accordance with embodiments of the present disclosure can have various other configurations.

As discussed above, in some embodiments, the housing can include more than two compartments. The compartments can be separated by a divider that is configured to be at least partially broken, removed, open or otherwise changed to allow the interiors of the compartments to communicate and the contents of the compartments to mix. In some embodiments, as discussed above, the housing can include more than two compartments and/or other features (e.g., layers) that allow generation and release of hydrogen in a controllable manner. FIGS. 5A-5C illustrate an embodiment in which a hydrogen-delivering system 500 includes a housing 502 having multiple compartments, such as first, second, third, and forth compartments 510, 512, 516, 518 that have their interiors separated from one another when the system 500 is a non-activated state (i.e., when it is not generating hydrogen). In this example, the first compartment includes an aqueous composition 506, and each of the second, third, and forth compartments 512, 516, 518 includes at least one respective dry compound 504a, 504b, 504c. It should be noted that the dry compounds 504a, 504b, 504c can be the same or different compounds and they are capable of entering into a hydrogen-generating and/or hydrogen-releasing reaction with the aqueous composition 506. Also, the aqueous composition 506 can be in the form of capsules having the aqueous composition releasably encapsulated therein, or in the form of other element(s).

The system 500 can be activated in a suitable manner, for example, using one or more activation features (not shown), including more than one activation feature, which can be activation feature(s) of different types. In this example, the system 500 can be activated in a sequential manner, such that the hydrogen is generated or released (if one or more of the compounds is a hydrogen-storing compound) at various times. In some embodiments, at least a portion of the housing 502 can be pressure-sensitive, such that applying pressure thereto (manually or in another manner) causes activation of the enclosed chemical compounds and hydrogen generation.

Thus, FIG. 5A shows the system 500 in a non-activated state in which the first, second, third, and forth compartments 510, 512, 516, 518 have their interior separated from one another. In this example, it is shown for illustration purposes only that the second and third compartments 512, 516 are separated by a first divider member or divider 514, and third and fourth compartments 516, 518 are separated by a second divider member or divider 520. The first and second dividers 514, 520 can be removable, disintegrable, or they can be configured to otherwise change their configurations to allow the interiors of the respective compartments to communicate. The first and second compartments 510, 512 are also separated from one another when the system 500 is in the non-activated state, and, in this example, the first and second compartments 510, 512 are shown to be separated by a third divider 511 which can be a different divider than the first and second dividers 514, 520. However, it should be appreciated that, in some embodiments, the first, second, and third dividers 514, 520, 511 can be the same type of elements that are configured to be at least partially removed. The dividers can be in the form of membranes, seals, common walls, or any other types of at least partially removable dividers. It should be noted that the dividers are referred to as "first," "second," and "third" for the description purposes only and not to indicate any particular order.

In use, the housing 502 can be positioned on the target area of the subject's skin and it can be affixed to the skin using one or more attachment elements (not shown), e.g., any of the attachment elements 108, 208, 308, or attachment element(s) of any suitable type. The activation of the system 500 can begin prior to, simultaneously with, or after the housing 502 is attached to the skin. As shown in FIG. 5B, when the system 500 is activated, the contents of the first and second compartments 510, 512 (the aqueous composition 506 and the dry chemical compound(s) 504a) mix thereby molecular hydrogen (not shown) can be generated and released through the sides of the first and second compartments 510, 512 on the skin-facing surface 503 of the housing 502.

After at least a portion of the aqueous composition 506 initially enclosed within the first compartment 510 reaches the second compartment 512 and the hydrogen-generating reaction (or hydrogen release) occurs, the first divider 514 can be at least partially removed. This can be done using an activation feature. As another variation, in some embodiments, the first divider 514 can be a degradable or dissolvable divider that can at least partially disintegrate upon contact with the aqueous composition. In this way, in such implementations, when the aqueous composition 506 is transferred into the second compartment 512, the divider 514 is exposed to moisture and begins to disintegrate, as shown schematically in FIG. 5C. This causes the aqueous composition 506 to penetrate into the third compartment 516, as also shown by arrow 517 in FIG. 5C, which causes the aqueous composition 506 to react with the dry chemical compound(s) 504b and thereby generate molecular hydrogen. In some embodiments, the first divider 514 can have properties and it can be positioned within the housing 502 such that it begins to disintegrate after substantially the entire hydrogen that the aqueous composition 506 and the dry chemical compounds 504a are capable of generating is generated and delivered to the subject. In this way, the third compartment 516 can begin emitting hydrogen, on the skin-facing side 503 of the housing 502, after the first and second compartments 510, 512, and another area of the subject's skin can thus be treated. The third divider 511 can be similar or different than the second divider 514 and it can be configured to be changed (e.g., broken, removed, disintegrated, etc.) to allow the interiors of the third and fourth compartments 516, 518 communicate so that their contents mix and generate molecular hydrogen. Thus, a certain spatial delivery of the topical hydrogen therapy can be achieved.

It should further be appreciated that the housing 502 is shown in FIGS. 5A to 5C to include four compartments by way of example only, as any other number of compartments (e.g., three or greater than four), which can be arranged in various regular and/or irregular patterns, can be formed. Also, while one of the compartments (510) is shown in FIGS. 5A to 5C to include the aqueous composition 506, a system can be made having more than one of its compartments including the liquid composition 506.

It should further be appreciated that in FIGS. 5A-5C the relative sizes of the components of the housing 502 are shown for illustration purposes only. For example, the first compartment 510 (having the aqueous composition enclosed therein) can be larger than at least one or all of the second, third, and fourth compartments 512, 516, 518. Also, the compartments can have various shapes and they can be arranged differently with respect to one another. For example, in some embodiments, the compartment enclosing the liquid composition can be disposed above (i.e., further away from the skin-facing surface) one or more compartments storing at least one dry hydrogen-generating chemical. Alternatively, a liquid composition-enclosing compartment can be disposed adjacent to the skin-facing surface of the system, and, in some embodiments, it can at least partially protrude from the skin-facing surface (e.g., similar to a capsule in embodiments described in connection with FIGS. 2C and 2E).

In the described embodiments, a mixture of chemicals or substance with hydrogen storage is initially in a dry state. In the dry mixture, no reaction occurs and no hydrogen is generated. In this form, the hydrogen-generating system or device can be safely transported and stored. The system is configured such that a liquid composition is delivered into the housing and/or caused to come in contact with the dry chemicals thereby activating a chemical reaction in which molecular hydrogen is generated. It should be appreciated that the system can be configured to be activated to generate molecular hydrogen in various ways. For example, its housing can be subjected to application of pressure, as discussed above. In some implementations, the housing can be configured to activate the hydrogen-generating reaction by shaking, bending, squeezing, or otherwise manipulating the housing. The hydrogen-generating system can be included in a suitable package such that, prior to use, the system is protected from being activated.

The hydrogen generating and delivering system in accordance with embodiments of the present disclosure can have various modifications. For example, in some embodiments, the hydrogen-generating system can be associated with a feature, such as an indicator (e.g., a timer), that allows to visually or otherwise determine that the delivery of hydrogen is completed. In this way, the subject or another person administering the system to the subject's skin can know when to remove the system from the target area. Also, in some implementations, the system can include or can be associated with more than one indicators configured to indicate, for example, that a delivery of hydrogen from a certain portion of the system is completed.

The dry compounds 104 (FIGS. 1A and 1B), 204 (FIGS. 2A and 2B), 204' (FIG. 2C), 214 (FIG. 2D), 224 (FIG. 2E), 304 (FIGS. 3A and 3B), 404 (FIGS. 4A and 4B), 504, 504$b$, 504$c$ (FIGS. 5A to 5C), or any other dry chemical(s), can comprise any suitable chemical(s). Various materials, including nanomaterials and biopolymers, can releasably store hydrogen, and the hydrogen-generating system in accordance with embodiments of the present disclosure can rely on a suitable chemical reaction to generate hydrogen. For example, the reactions of the electrochemical series of elements (Ca, Mg, Al, Zn, and Fe) with water, acids, or bases can generate molecular hydrogen. In the described embodiments, the chemicals that ensure safety, ecological compatibility, stability to long-term storage, and other beneficial properties, are used. The reagents are selected that do not cause burns and other unpleasant consequences for patients if the housing is unintentionally broken.

Without loss of generality, below are examples of preparing chemicals for the generation of molecular hydrogen in a housing of a hydrogen-generating system in accordance with some embodiments of the present disclosure.

EXAMPLES

Example 1

The housing (e.g., a plastic container) includes a metallic aluminum (e.g., foil or powder) that is covered by aluminum oxide. A water suspension of calcium hydroxide, $Ca(OH)_2$ ("slaked lime"), when in contact with the metallic aluminum covered by aluminum oxide, activates the following set of chemical reactions:

$$Al_2O_3 + 3Ca(OH)_2 = Ca_3(AlO_3)_2 + 3H_2O,$$

$$2Al + 6H_2O = 2Al(OH)_3 + 3H_2\uparrow,$$

$$2Al + 3Ca(OH)_2 = Ca_3(AlO_3)2 + 3H_2\uparrow, \text{ and}$$

$$2Al(OH)_3 + Ca(OH)_2 = Ca[Al(OH)_4]2, \text{ where the arrow } \uparrow \text{ indicates release of molecular hydrogen.}$$

Example 2

The housing includes a metallic aluminum (e.g., foil or powder) that is covered by aluminum oxide. A water solution of $CuSO_4$ and $NaCl$, when in contact with the metallic aluminum covered by aluminum oxide, activates a set of non-stoichiometric reactions:

$$2Al + 6H_2O \Rightarrow 2Al(OH)_3 + 3H_2\uparrow$$

$$2Al + 3CuSO_4 \Rightarrow Al_2(SO_4)_3 + 3Cu\downarrow$$

$$CuSO_4 + 2NaCl \Leftrightarrow CuCl_2 + Na_2SO_4$$

$$CuCl_2 + Al \Rightarrow AlCl_3 + Cu\downarrow,$$

where the arrow ↑ indicates release of molecular hydrogen.

In this example, the reaction occurs with the release of heat and the formation of hydrogen. The release of heat can be beneficial in some cases, since the heat can have a placebo effect on the subject (e.g., a human patient). Furthermore, in some embodiments, the heat can have, in combination with the release of hydrogen, a therapeutic effect.

Molecular hydrogen generated by a hydrogen-delivering system in accordance with some embodiments of the present disclosure can be used to treat various conditions. For example, it can be used for treatment of burns, psoriasis, eczema, and various other skin conditions. The hydrogen gas can also be topically applied to treat or prevent inflammation, minor cuts, muscle sprain, ligament strain, tendonitis, and other injuries. The described systems and methods can be used for $H_2$ therapy for alleviating symptoms of psoriasis, eczema, arthritis, burns, rosacea and various other skin conditions. Because of its powerful anti-oxidant properties, $H_2$ can also be used for anti-ageing properties, for example, in the form of a face mask or another form suitable for application to the face, neck, hands, chest, or other areas of the body.

In the present disclosure, the subject can be a human or a non-human subject.

Since other modifications and changes varied to fit particular operating requirements and environments will be apparent to those skilled in the art, the invention is not considered limited to the examples chosen for purposes of disclosure, and covers all changes and modifications which do not constitute departures from various embodiments, or combinations of the embodiments, of the invention.

In some embodiments, for improved contact with the skin, the skin surface or the skin-facing surface of the housing can be treated with a compound such as, e.g., a moisturizing cream or a disinfectant liquid. The compound is selected such that its application does not affect or prevent diffusion of hydrogen into the skin or other tissues.

EQUIVALENTS

While the present disclosure has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not patentable in view of such publications.

As used herein, all headings are simply for organization and are not intended to limit the disclosure in any manner. The content of any individual section may be equally applicable to all sections.

What is claimed is:

1. A hydrogen-generating system for external use on a subject, comprising:
    a housing having enclosed therein:
        a first portion comprising an aluminum powder and calcium hydroxide ($Ca(OH)_2$) powder enclosed within gauze or porous paper, and
        a second portion, separate from the first portion and comprising an inlet configured to receive an aqueous composition and a sealing element suitable for sealing the inlet after receiving the aqueous composition
    wherein the housing has a first surface configured to be positioned adjacent to the subject's skin, the first surface being at least partially hydrogen-permeable and impermeable to the aluminum powder, the calcium hydroxide ($Ca(OH)_2$) powder, and the aqueous composition; and
    at least one attachment element configured to attach the housing to a surface of the subject's skin,
    wherein the housing is configured to be activated to cause the aqueous composition to come in contact with and react with the aluminum powder and the calcium hydroxide ($Ca(OH)_2$) powder to thereby cause generation of molecular hydrogen that passes through the first surface and is delivered to the subject's skin.

2. The system of claim 1, wherein the aqueous composition is water, or a suitable acid or base.

3. The system of claim 1, wherein the at least one attachment element is at least partially adhesive.

4. The system of claim 1, wherein a second surface of the housing that is opposite to the first surface is hydrogen-impermeable.

5. The system of claim 1, wherein portions of an outer wall of the housing that are different from the first surface are hydrogen-impermeable.

6. The system of claim 1, wherein the housing has a shape that conforms to a shape of a joint of the subject's body.

7. A method of topical administration of molecular hydrogen, comprising:
    applying a hydrogen-delivering system to a target area of a subject's skin by positioning a skin-facing surface of a housing of the hydrogen-delivering system onto the target area, the housing having enclosed therein a first portion comprising aluminum powder and calcium hydroxide ($Ca(OH)_2$) powder enclosed within gauze or porous paper, and a second portion, separate from the first portion and comprising an inlet configured to receive an aqueous composition and a sealing element suitable for sealing the inlet after receiving the aqueous composition; wherein the skin-facing surface of the housing is at least partially hydrogen-permeable and impermeable to the aluminum powder, the calcium hydroxide ($Ca(OH)2$) powder, and the aqueous composition; and wherein the hydrogen-delivering system comprises at least one attachment element configured to attach the housing to a surface of the subject's skin and
    delivering the aqueous composition to at least partially contact the aluminum powder and the calcium hydroxide ($Ca(OH)_2$) powder within the housing and thereby generate molecular hydrogen, wherein the generated molecular hydrogen penetrates through at least one hydrogen-permeable portion of the skin-facing surface and is thereby administered to the target area of the subject's skin.

8. The method of claim 7, wherein the aqueous composition is water, or a suitable acid or base.

9. The method of claim 7, further comprising sealing the inlet after delivering the liquid composition.

10. The method of claim 7, wherein the molecular hydrogen is administered to the target area of the subject's skin for a duration of time that is from between about 10 minutes to about 8 hours.

* * * * *